United States Patent
Fakhrai et al.

(10) Patent No.: US 8,293,252 B2
(45) Date of Patent: Oct. 23, 2012

(54) UNIVERSAL TUMOR CELL VACCINE FOR ANTI CANCER THERAPEUTIC AND PROPHYLACTIC UTILIZATION

(75) Inventors: Habib Fakhrai, La Jolla, CA (US); Daniel L. Shawler, San Diego, CA (US)

(73) Assignee: Novarx Corporation, San Diego, CA (US)

( * ) Notice: Subject to any disclaimer, the term of this patent is extended or adjusted under 35 U.S.C. 154(b) by 0 days.

(21) Appl. No.: 12/520,485

(22) PCT Filed: Dec. 20, 2007

(86) PCT No.: PCT/US2007/088457
§ 371 (c)(1),
(2), (4) Date: Jun. 19, 2009

(87) PCT Pub. No.: WO2008/105978
PCT Pub. Date: Sep. 4, 2008

(65) Prior Publication Data
US 2010/0047289 A1    Feb. 25, 2010

Related U.S. Application Data

(60) Provisional application No. 60/876,222, filed on Dec. 20, 2006.

(51) Int. Cl.
*A61P 37/04* (2006.01)
(52) U.S. Cl. ...................................... 424/277.1
(58) Field of Classification Search ................ 424/277.1
See application file for complete search history.

(56) References Cited

U.S. PATENT DOCUMENTS

2002/0006413 A1 *   1/2002   Sobol et al. ............... 424/277.1

FOREIGN PATENT DOCUMENTS

| WO | WO-96/02143 | 2/1996 |
| WO | WO-01/54716 | 8/2001 |
| WO | WO-01/74404 | 10/2001 |
| WO | WO-02/12447 | 2/2002 |

OTHER PUBLICATIONS

Examiner's First Report on Patent Application No. AU 2007347689, mailed Jun. 7, 2012, 2 pages.

* cited by examiner

*Primary Examiner* — Lynn Bristol
(74) *Attorney, Agent, or Firm* — Morrison & Foerster LLP

(57) ABSTRACT

A universal tumor vaccine bearing antigens characteristic of each of a wide variety of tumors that may afflict a patient being treated comprises at least two different allogeneic cells that display a multiplicity of tumor associated antigens and also have been modified to inhibit the expression of a natively produced immunosuppressive agent such as TGFβ.

16 Claims, No Drawings

UNIVERSAL TUMOR CELL VACCINE FOR ANTI CANCER THERAPEUTIC AND PROPHYLACTIC UTILIZATION

CROSS-REFERENCE TO RELATED APPLICATIONS

This application is the national phase of PCT application PCT/US2007/088457 having an international filing date of Dec. 20, 2007, which claims the benefit of U.S. Provisional Application No. 60/876,222 filed Dec. 20, 2006 which are incorporated herein by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 563382000300Seqlist.txt | Nov. 9, 2010 | 664 bytes |

BACKGROUND OF THE INVENTION

1. Field of the Invention

The present invention relates generally to cancer therapy and more specifically to tumor vaccines.

2. Description of the Related Art

Vaccines are injections of substances designed to activate the patient's immune system in order to attack a specific target, such as a cancer cell. Scientists have experimented with using tumor cells as vaccines for the past 30 years. The theory is simple; vaccinate a cancer patient with tumor cells and the vaccine will induce an immune response that destroys tumor cells throughout the body. Unfortunately a major barrier called immunosuppression limits the efficacy of this technology. Immunosuppression happens because most tumor cells produce molecules that allow the cells to hide from the immune system, preventing the development of clinically effective immune responses.

The patented NovaRx technology helps to overcome this immunosuppressive barrier. We observed that a molecule called transforming growth factor-beta (TGF-β) is one of the most potent immunosuppressive molecules produced by tumor cells. Our technology blocks the immunosuppressive effects of TGF-β in the vaccine, rendering the vaccine more potent.

Our scientists were the first in the world to demonstrate that the innovation of blocking TGF-β rendered tumor cell vaccines more effective. In a study published in the prestigious scientific Journal Proceedings of the National Academy of Sciences, they showed that this technology was able to completely eradicate rapidly growing tumors in an animal model. They later extended this finding to the treatment of patients with glioma (brain cancer) and lung cancer. In other work, NovaRx researchers have also demonstrated that inoculation of colorectal cancer patients with allogeneic tumor cells induced immune responses that recognized and targeted the individual patients' tumor cells. However, because of the expression of immune suppressive in the vaccine cells therapeutic effects did not occur.

SUMMARY OF THE INVENTION

The invention provides a composition for stimulating an immune response in a patient having an adenocarcinoma, squamous, or other forms of cancers and is comprising a combination of allogeneic tumor cells and/or tumor stem cells that are selected on the basis of secreting at least one immunosuppressive agent, e.g., TGF-β, and that are genetically modified to reduce or inhibit the expression of said at least one immunosuppressive agent, e.g., TGF-β, and that collectively express a spectrum of tumor associated antigens representative of colon, breast, lung, prostate, pancreas, kidney, endometrium, cervix, ovary, thyroid, and other glandular tissue carcinomas, as well as tumors of central nervous system, melanoma, lymphoma and a physiologically acceptable carrier. The adenocarcinoma can be, for example, colon, breast, lung, prostate, pancreas, kidney, endometrium, cervix, ovary, thyroid, or other glandular tissue, as well as tumors of central nervous system, melanoma, lymphoma. The invention also provides a composition containing said combination of allogeneic tumor cells and an allogeneic cell expressing a cytokine or expressing an antibody that blocks specific molecules. The invention additionally provides a method of stimulating an immune response in a patient having colon, breast, lung, prostate, pancreas, kidney, endometrium, cervix, ovary, thyroid, or other glandular tissue cancer, as well as tumors of central nervous system, melanoma, lymphoma by administering to the patient said combination of allogeneic tumor cells, wherein the combination stimulates an immune response to autologous tumor cells in the patient. The method can further include an allogeneic cell such as a fibroblast genetically modified to express a cytokine or expressing an antibody that blocks specific molecules.

DETAILED DESCRIPTION OF THE PREFERRED EMBODIMENT

Unless defined otherwise, technical and scientific terms used herein have the same meaning as commonly understood by one of ordinary skill in the art to which this invention belongs. See, e.g., Singleton P and Sainsbury D., Dictionary of Microbiology and Molecular Biology 3rd ed., J. Wiley & Sons, Chichester, N.Y., 2001.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

The invention provides compositions and methods for stimulating an immune response in a patient having an adenocarcinoma or other cancers using allogeneic tumor cells and/or tumor stem cells. The compositions and methods of the invention are particularly useful for stimulating an immune response in a patient having for example, colon, breast, lung, prostate, pancreas, kidney, endometrium, cervix, ovary, thyroid, or other glandular tissue cancer, as well as squamous, melanoma, central nervous system, and lymphomas. The allogeneic tumor cells and/or tumor stem cells can be genetically modified to enhance an immune response. The allogeneic vaccine can further include an allogeneic cell genetically modified to express a cytokine or express an antibody that blocks other immune inhibitory molecules. The invention also provides methods of stimulating an immune response in a patient having cancers of different types including an adenocarcinoma, including a patient having for example, colon, breast, lung, prostate, pancreas, kidney, endometrium, cervix, ovary, thyroid, or other glandular tissue cancer, as well as squamous, melanoma, central nervous system, and lymphomas by administering one or more allogeneic tumor cells, and or tumor stem cells wherein the allogeneic tumor cell stimulates an immune response to an autologous tumor cell in the patient.

The methods of the invention are advantageous in that they utilize one or more allogeneic tumor cells and or tumor stem cells expressing antigens that are expressed in a patient having an adenocarcinoma, for example, colon, breast, lung, prostate, pancreas, kidney, endometrium, cervix, ovary, thyroid, or other glandular tissue adenocarcinoma, as well as squamous, melanoma, central nervous system, and lymphomas thereby stimulating an immune response to the antigens. The use of allogeneic tumor cells and/or tumor stem cells provides a generic source of antigen that can be administered to a variety of patients, in contrast to using autologous tumor cells, which must be isolated from each individual patient. The methods of the invention are advantageous in that the allogeneic cells and/or tumor stem cells are suitable as a cancer vaccine and can stimulate an immune response against autologous tumor cells of a cancer patient.

As used herein, an "autologous cell" refers to a cell derived from a specific individual. In methods of the invention, the specific individual from which an autologous cell is derived refers to an individual administered an allogeneic vaccine of the invention. As used herein, an "autologous tumor cell" refers to a cell derived from a tumor in such an individual.

As used herein, an "allogeneic cell" and/or "tumor stem cells" refers to a cell that is not derived from the individual administered an invention vaccine, that is, has a different genetic constitution than the individual. An allogeneic cell and/or tumor stem cells is generally obtained from the same species as the individual administered an invention vaccine. In particular, a human allogeneic cell can be used to stimulate an immune response in a human individual having cancer. As used herein, an "allogeneic tumor cell and/or tumor stem cells" refers to a tumor cell that is not derived from the individual to which the allogeneic cell is to be administered. An allogeneic tumor cell and/or tumor stem cells expresses at least one tumor antigen that is common to an autologous tumor cell in a patient. Generally, the allogeneic cell and/or tumor stem cell is derived from a similar or different type of tumor as that being treated in the patient. For example, as disclosed herein, a patient being treated for a, for example, colon, breast, lung, prostate, pancreas, kidney, endometrium, cervix, ovary, thyroid, or other glandular tissue cancer as well as squamous, melanoma, central nervous system, and lymphomas can be administered an allogeneic tumor cell derived from a, for example, colon, breast, lung, prostate, pancreas, kidney, endometrium, cervix, ovary, thyroid, or other glandular tissue, as well as squamous, melanoma, central nervous system, and lymphomas tumor sharing common antigens or tumor stem cells isolated from one tumor and guided to differentiate into a different type tumor by utilizing stem cell factors and conditioned media from tumors similar to the target tumor. Utilization of the latter procedure can result in tailor making a vaccine to an individual.

Although an allogeneic tumor cell and/or tumor stem cell can be derived from a, for example, colon, breast, lung, prostate, pancreas, kidney, endometrium, cervix, ovary, thyroid, or other glandular tissue tumor, as well as squamous, melanoma, central nervous system, and lymphomas the methods of the invention can also utilize an allogeneic cell and or tumor stem cell expressing one or more tumor antigens. For example, an allogeneic cell and or tumor stem cell can be guided or engineered to express one or more tumor antigens specific for a particular tumor. For example, to treat a, for example, colon, breast, lung, prostate, pancreas, kidney, endometrium, cervix, ovary, thyroid, or other glandular tissue carcinoma, as well as squamous, melanoma, central nervous system, and lymphomas a cell can be genetically engineered to express tumor antigens expressed in a, for example, colon, breast, lung, prostate, pancreas, kidney, endometrium, cervix, ovary, thyroid, or other glandular tissue, as well as squamous, melanoma, central nervous system, and lymphomas respectively, carcinoma. Exemplary tumor antigens suitable for an allogeneic tumor cell for treatment of a, for example, colon, breast, lung, prostate, pancreas, kidney, endometrium, cervix, ovary, thyroid, or other glandular tissue carcinoma as well as squamous, melanoma, central nervous system, and lymphomas include, for example, carcinoembryonic antigen (CEA), MUC-1, Ep-CAM, HER-2/neu, p53, and MAGE, including MAGE 1, 2, 3, 4, 6 and 12. Additional tumor antigens can also be expressed in an allogeneic cell and used in an allogeneic vaccine of the invention. Additional tumor antigens can be identified using well known methods of screening for tumor antigens using, for example, tumor specific antibodies. Additional tumor antigens can be cloned into an allogeneic cell and expressed. Methods of genetically engineering a cell to express a particular gene is well known to those skilled in the art (see Sambrook et al., Molecular Cloning: A Laboratory Manual, 2nd ed., Cold Spring Harbor Press, Plainview, N.Y. (1989); Ausubel et al., Current Protocols in Molecular Biology (Supplement 47), John Wiley & Sons, New York (1999)).

In addition to, for example, colon, breast, lung, prostate, pancreas, kidney, endometrium, cervix, ovary, thyroid, or other glandular tissue cancer, as well as squamous, melanoma, central nervous system, and lymphomas an invention vaccine can be used to treat an individual having other types of cancers. Because many adenocarcinomas share antigens, as described in more detail below, an invention vaccine used to treat one type of adenocarcinoma can also be used to treat other types of adenocarcinomas if the tumors share antigens with the allogeneic tumor cell of an invention vaccine. Similarly, other types of tumors having shared antigens can be treated with an invention vaccine. As used herein, a "patient having an adenocarcinoma" refers to an individual having signs or symptoms associated with an adenocarcinoma. An adenocarcinoma is a malignant neoplasm of epithelial cells in glandular or glandlike pattern. Exemplary adenocarcinomas include those of colon, breast, lung, prostate, pancreas, kidney, endometrium, cervix, ovary, thyroid, or other glandular tissues.

As used herein, a "patient having colon, breast, lung, prostate, pancreas, kidney, endometrium, cervix, ovary, thyroid, or other glandular tissue cancer as well as squamous, melanoma, central nervous system, and lymphomas" refers to an individual having signs or symptoms associated with colon, breast, lung, prostate, pancreas, kidney, endometrium, cervix, ovary, thyroid, or other glandular tissue cancer as well as squamous, melanoma, central nervous system, and lymphomas. There is a wide variety of medical tests that are used to detect cancer and they use different methods to recognize and locate cancer. Some cancer techniques, such as mammography and colonoscopy, are used to detect specific cancer types. Others are more general and are able to detect a variety of different cancer types. One skilled in the art can readily determine if an individual has signs or symptoms of colon, breast, lung, prostate, pancreas, kidney, endometrium, cervix, ovary, thyroid, or other glandular tissue cancer as well as squamous, melanoma, central nervous system, and lymphomas.

As used herein, an "immune response" refers to a measurable response to an antigen mediated by one or more cells of the immune system. An immune response can include a humoral or cellular response. As used herein, an immune response to an autologous tumor cell antigen refers to a measurable immune response to at least one antigen expressed on an autologous tumor cell. Similarly, an immune response to an autologous tumor cell refers to an immune response that is detectable and specific for an autologous tumor cell. As disclosed herein, use of an invention allogeneic vaccine in a colon, breast, lung, prostate, pancreas, kidney, endometrium, cervix, ovary, thyroid, or other glandular tissue carcinoma, as well as squamous, melanoma, central nervous system, and lymphomas patient results in a detectable immune response to autologous tumor cells.

As used herein, a "cytotoxic T lymphocyte response" or "CTL response" refers to an immune response in which cytotoxic T cells are activated. A CTL response includes the activation of precursor CTLs as well as differentiated CTLs. For example, as disclosed herein, administering a vaccine containing allogeneic carcinoma cells increases the frequency of precursor CTLs specific for tumor antigens of the allogeneic cells. The vaccine also stimulates the frequency of CTLs for autologous tumor cells.

As used herein, a CTL response is intended to include any measurable CTL response for a particular antigen. Preferably, the CTL response includes at least one CTL that is specific for an antigen expressed on an autologous tumor cell. The level of CTL response can range from a modest response to an intermediate response as well as a strong CTL response. Even a modest response can be effective in treating a cancer patient if such treatment stimulates an immune response against autologous tumor cells in the patient.

As disclosed herein, an allogeneic tumor cell vaccine increases the frequency of precursor CTLs in a patient administered the vaccine. The allogeneic vaccine stimulates a 5- to 10-fold increase in the frequency of precursor CTLs. It is understood that any increase in CTL response is considered a stimulated CTL response so long as the CTL response is against at least one antigen associated with an autologous tumor in the patient.

As used herein, an exogenous cytokine refers to a cytokine that is administered to an individual. For example, an exogenous cytokine can be administered as a cytokine composition, or the cytokine can be administered as a cell that expresses a cytokine.

The allogeneic tumor cell vaccine of the invention can be administered with an allogeneic cell expressing a cytokine. The cytokine-expressing allogeneic cell can be a non-tumor cell such as a fibroblast or a tumor cell. For example, as disclosed herein, a cytokine-expressing allogeneic fibroblast cell genetically modified to express IL-2 is administered as a component of an allogeneic tumor cell vaccine. Cytokines useful in methods of the invention are those that enhance an immune response to a tumor antigen. Exemplary cytokines include interleukin-1 (IL-1), IL-2, IL-3, IL-4, IL-5, IL-6, IL-12, gamma-interferon, and granulocyte macrophage-colony stimulating factor (GM-CSF). If desired, the cytokine can be expressed in various functional forms so long as the cytokine retains activity to enhance an immune response. For example, a cytokine such as GM-CSF can function in a soluble or membrane-bound form. Particularly useful cytokines for use in an allogeneic tumor cell vaccine of the invention are IL-2 and GM-CSF. Methods for modifying cells to express a cytokine for stimulating an immune response are well known to those skilled in the art. Exemplary of expressing an antibody in the tumor vaccine or tumor stem cell vaccine is an antibody that inhibits PGE2 or CTLA4. These molecules can be expressed in the engineered vaccine cells or in a different set of allogeneic cells such as an allogeneic fibroblast which is mixed with the tumor cell vaccine.

A cytokine-expressing allogeneic cell can be any carrier cell that provides a sufficient level of cytokine expression to enhance an immune response. As used herein, an enhanced immune response is any measurable increase in an immune response. Essentially any cell type that provides sufficient expression of a cytokine to enhance an immune response can be used in methods of the invention. Particularly useful allogeneic cells for expressing a cytokine include allogeneic fibroblast cells and allogeneic tumor cells. Methods of genetically modifying an allogeneic cell to express a cytokine are well known to those skilled in the art (Sambrook et al., supra, 1989; Ausubel et al., supra, 1999). For example, a fibroblast cell is genetically modified to express IL-2.

Additionally, allogeneic tumor cells and or tumor stem cells can be modified to express a cytokine. An allogeneic tumor cell or tumor stem cell expressing antigens common to a tumor in a patient can be genetically modified to express a cytokine or an antibody the blocks immune inhibitors. For example, in a colon, breast, lung, prostate, pancreas, kidney, endometrium, cervix, ovary, thyroid, or other glandular tissue cancer patient, as well as squamous, melanoma, central nervous system, and lymphomas an allogeneic colon, breast, lung, prostate, pancreas, kidney, endometrium, cervix, ovary, thyroid, or other glandular tissue, as well as squamous, melanoma, central nervous system, and lymphomas respectively, cancer cell can be genetically modified to express a cytokine or an antibody that blocks immune inhibitors, with the allogeneic cell expressing antigens common to a tumor in a patient. If desired, the cytokine expressing tumor cell and or tumor stem cells can be genetically modified with additional molecules useful for stimulating or enhancing an immune response, for example, B7.1 and B7.2. The cytokine expressed in the allogeneic cell can be any cytokine that enhances an immune response, including those disclosed herein. Particularly useful cytokines for use in methods of the invention include IL-2 and GM-CSF and particular antibodies are antibodies that inhibit PGE2 or CTLA4. In the case where the cytokine and/or antibody is expressed in an allogeneic tumor cell, GM-CSF can be expressed in the membrane-bound form to enhance an immune response to tumor antigens of the allogeneic tumor cell.

As used herein, a physiologically acceptable carrier useful in invention vaccines refers to any of the well known components useful for immunization. The components of the physiological carrier are intended to facilitate or enhance an immune response to an antigen administered in a vaccine. The formulations can contain buffers to maintain a preferred pH range, salts or other components that present the antigen to an individual in a composition that stimulates an immune response to the antigen. The physiologically acceptable carrier can also contain one or more adjuvants that enhance the immune response to the antigen. Formulations can be administered subcutaneously, intramuscularly, intradermally, or in any manner acceptable for immunization.

As used herein, the term "adjuvant" refers to a substance which, when added to an immunogenic agent such as an allogeneic tumor cell, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides. Adjuvants can also include, for example, squalene mixtures (SAF-I), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (IS-COMs). For veterinary use and for production of antibodies in animals, mitogenic components of Freund's adjuvant (both complete and incomplete) can be used. In humans, Incomplete Freund's Adjuvant (IFA) is a preferred adjuvant. Various appropriate adjuvants are well known in the art. Additional adjuvants include, for example, bacille Calmett-Gerin (BCG), DETOX (containing cell wall skeleton of *Mycobacterium phlei* (CWS) and monophosphoryl lipid A from *Salmonella* Minnesota (MPL)), and the like.

Furthermore, a cytokine or an antibody that blocks immune inhibitors can also be used as an adjuvant to enhance an immune response, as described herein. In particular, the methods of the invention can advantageously use a vaccine containing allogeneic tumor cells and an allogeneic cell genetically modified to express a cytokine such as IL-2, GM-CSF, or other cytokines, as well as antibodies such as antibodies that inhibits PGE2 or CTLA4 as disclosed herein. The use of cytokine expressing cells allows enhancement of the immune response to antigens of the allogeneic tumor cells, as described herein. It is understood that more than one cytokine can be administered, if desired, either directly administering one or more cytokines or administering cytokines as a cell expressing multiple cytokines or multiple cells expressing multiple cytokines, or combinations thereof.

The invention provides a composition for stimulating an immune response in a patient having an adenocarcinoma. For example, the invention provides a composition for stimulating an immune response in a patient having colon, breast, lung, prostate, pancreas, kidney, endometrium, cervix, ovary, thyroid, or other glandular tissue cancer as well as squamous, melanoma, central nervous system, and lymphomas. The composition contains one or more allogeneic tumor cells and or tumor stem cell and a physiologically acceptable carrier. The invention also provides a composition of matter containing the cells alone. The invention further provides a composition containing one or more allogeneic tumor cells, an allogeneic fibroblast cell genetically modified to express a cytokine such as IL-2 or GM-CSF, and a physiologically acceptable carrier. In addition, other allogeneic tumor cells, as disclosed herein, can be included in an invention composition for stimulating an immune response.

As disclosed herein, the allogeneic tumor cells and/or tumor stem cells can be genetically modified to express molecules that enhance an immune response. For example, the allogeneic cells can be modified to express B7.1 and B7.2. Furthermore, as described above, the allogeneic tumor cells can be modified to express a cytokine.

The allogeneic tumor cells and/or tumor stem cells are administered at a dose sufficient to stimulate an immune response to one or more antigens of the allogeneic tumor cell that are common to an autologous tumor in a patient. One skilled in the art can readily determine an appropriate dose range for administering sufficient allogeneic tumor cells to elicit an immune response. Such a dose can be at least about $1\times10$ to the power of 2 cells, about $1\times10$ to the power of 3 cells, about $1\times10$ to the power of 4 cells, about $1\times10$ to the power of 5 cells, about $1\times10$ to the power of 6 cells, about $1\times10$ to the power of 7 cells, about $1\times10$ to the power of 8 cells, about $1\times10$ to the power of 9 cells, or about $1\times10$ to the power of 10 cells, or more. For example, as disclosed herein, allogeneic tumor cells administered at a total dose of about $6\times10$ to the power of 7 cells is sufficient to stimulate a CTL response. If more than one allogeneic tumor cell is administered, each cell can be administered at an individual dose so that an appropriate total dose of cells is administered.

The invention also provides a method of stimulating an immune response in a patient having an adenocarcinoma. For example, the invention provides a method of stimulating an immune response in a patient having colon, breast, lung, prostate, pancreas, kidney, endometrium, cervix, ovary, thyroid, or other glandular tissue cancer as well as squamous, melanoma, central nervous system, and lymphomas. The method can include the step of administering to the patient one or more allogeneic tumor cells, wherein the allogeneic cell stimulates an immune response to an autologous tumor cell in the patient. The administration of allogeneic tumor cells are advantageous for stimulating an immune response against a tumor in a patient without the need for isolating cells from the patient to generate such a tumor vaccine.

The invention additionally provides a method of stimulating an immune response in a patient having an adenocarcinoma, including a patient having colon, breast, lung, prostate, pancreas, kidney, endometrium, cervix, ovary, thyroid, or other glandular tissue cancer as well as squamous, melanoma, central nervous system, and lymphomas. The method includes the step of administering to the patient one or more allogeneic tumor cells, wherein the allogeneic cells stimulate a cytotoxic T lymphocyte (CTL) response to autologous tumor cells in the patient.

The invention additionally provides a method of stimulating a prophylactic anti cancer immune response in individuals vaccinated with the engineered tumor cell and/or tumor stem cell vaccine that will protect them against developing adenocarcinoma, including a patient having colon, breast, lung, prostate, pancreas, kidney, endometrial, cervix, ovary, thyroid, or other glandular tissue cancer as well as squamous, melanoma, central nervous system, and lymphomas. The method includes the step of administering to the individuals one or more engineered allogeneic tumor cells and or tumor stem cells, wherein the allogeneic cells stimulate a cytotoxic T lymphocyte (CTL) response to tumor cells that may arise in the individuals.

The invention additionally provides a method of stimulating a prophylactic anti cancer immune response in individuals vaccinated with the engineered tumor cell and/or tumor stem cell vaccine that will protect them against occult tumors or that may be at risk of developing adenocarcinoma, including a patient having colon, breast, lung, prostate, pancreas, kidney, endometrial, cervix, ovary, thyroid, or other glandular tissue cancer as well as squamous, melanoma, central nervous system, and lymphomas. The method includes the step of administering to the individuals one or more engineered allogeneic tumor cells and or tumor stem cells, wherein the allogeneic cells stimulate a cytotoxic T lymphocyte (CTL) response to tumor cells that may arise in the individuals or be present in an occult state.

The number of different allogeneic tumor cells to be administered can be varied depending on the particular needs of the vaccine. For example, a CTL response can be stimulated by one or more allogeneic tumor cells, two or more, three or more, four or more, five or more, six or more, seven or more, eight or more, nine or more, or even ten or more allogeneic tumor cells, if desired. The number of different allogeneic tumor cells to be administered can be readily determined by one skilled in the art by administering a variable number of tumor cells and lines and determining if an immune response is stimulated or an immune response is enhanced.

Exemplary allogeneic tumor cells and/or tumor stem cells useful in the invention include those obtained from established cancer cell lines and from tumor cell lines established from cancer biopsies.

The invention provides a method of stimulating an immune response in a patient having different cancers including a patient having an adenocarcinoma, whereby a CTL response to autologous non-tumor cells is minimized. For example, an invention method can be used to stimulate an immune response in a colon, breast, lung, prostate, pancreas, kidney, endometrium, cervix, ovary, thyroid, or other glandular tissue cancer patient. The methods of the invention are advantageous in that the allogeneic vaccine stimulates a CTL response against autologous tumor cells of the patient while minimizing a CTL response to non-tumor cells. In particular, the invention allogeneic vaccine resulted in a minimal CTL response to peripheral blood mononuclear cells (PBMC). As used herein, a "minimized" CTL response, when used in reference to autologous non-tumor cells, refers to a CTL response against autologous non-tumor cells that is undetectable or has little or no adverse effect on the patient.

The methods of the invention are directed to treating an individual having an adenocarcinoma, including a patient having colon, breast, lung, prostate, pancreas, kidney, endometrium, cervix, ovary, thyroid, or other glandular tissue cancer as well as squamous, melanoma, central nervous system, and lymphomas. As such, the allogeneic tumor cells useful in the invention are generally adenocarcinoma cells since such cells express a variety of adenocarcinoma antigens. For example, the allogeneic tumor cells can be colon, breast, lung, prostate, pancreas, kidney, endometrium, cervix, ovary, thyroid, or other glandular tissue cancer cells as well as squamous, melanoma, central nervous system, and lymphomas having shared antigens with other colon, breast, lung, prostate, pancreas, kidney, endometrium, cervix, ovary, thyroid, or other glandular tissue, as well as squamous, melanoma, central nervous system, and lymphomas respectively, carcinoma antigens.

Colon carcinoma, which is one of the most common forms of cancer, is an ideal candidate for the development of adjuvant immunotherapeutic approaches. While most patients with colon cancer are treated by tumor resection and do not exhibit clinically detectable disease immediately following surgery, many eventually relapse with disease in the liver or abdomen due to the presence of undetectable, disseminated microscopic metastases. The relative chemotherapy resistance of these recurrent colon cancer metastases further emphasizes the need for new treatment modalities, such as adjuvant immunotherapy.

As disclosed herein, an allogeneic colon, breast, lung, prostate, pancreas, kidney, endometrium, cervix, ovary, thyroid, or other glandular tissue cancer, as well as squamous, melanoma, central nervous system, and lymphomas cell line vaccine genetically modified to reduce or inhibit the expression of an otherwise secreted at least one immunosuppressive agent, e.g., TGF-β, is developed and characterized. The tumor cells and lines selected for inclusion in the vaccine are chosen on the basis of their secretion of at least one immunosuppressive agent, e.g., TGF-β, genetic modification to reduce or inhibit the expression of said at least one immunosuppressive agent, e.g., TGF-β, and the expression of a spectrum of tumor associated antigens (TAAs) representative of colon, breast, lung, prostate, pancreas, kidney, endometrium, cervix, ovary, thyroid, or other glandular tissue carcinomas, as well as squamous, melanoma, central nervous system, and lymphomas. In another embodiment, vaccination of colon, breast, lung, prostate, pancreas, kidney, endometrium, cervix, ovary, thyroid, or other glandular tissue cancer, as well as squamous, melanoma, central nervous system, and lymphomas patients with these tumor cells and/or tumor stem cell lines, combined with IL-2 secreting autologous cells, induces CTLs reactive with the patient's autologous tumor.

In addition to patients having colon, breast, lung, prostate, pancreas, kidney, endometrium, cervix, ovary, thyroid, or other glandular tissue cancer, as well as squamous, melanoma, central nervous system, and lymphomas the principles of an allogeneic tumor cell vaccine can similarly be applied to other types of cancers such as melanoma, brain and the like. The methods of the invention are particularly useful for treatment of adenocarcinomas, including colon, breast, lung, prostate, pancreas, kidney, endometrium, cervix, ovary, thyroid, or other glandular tissue, as well as squamous, melanoma, central nervous system, and lymphomas. For each type of cancer to be treated, the vaccine can contain allogeneic tumor cells and or tumor stem cells expressing antigens common to the type of cancer to be treated. In addition, a vaccine can contain allogeneic tumor cells of a different tumor type than that of the patient being treated. For example, a vaccine containing allogeneic colon carcinoma cells, such as those disclosed herein, can be used in a vaccine for stimulating an immune response in a patient having an adenocarcinoma, for example, of breast, lung, prostate, pancreas, kidney, endometrium, cervix, ovary, thyroid, or other glandular tissue, and the like. Such a vaccine is useful because the allogeneic tumor cells share common antigens in different types of tumors. For example, breast and lung adenocarcinomas, as well as colon carcinoma, express CEA, as described herein.

In addition to a vaccine containing allogeneic tumor cells alone, the invention also provides methods in which the allogeneic tumor cells are administered with a cytokine adjuvant. The allogeneic tumor cell vaccine can include administering a cytokine such as IL-2, GM-CSF or other cytokines, or an antibody that inhibits immune suppressor molecules, such as PGE2 and CTLA4 as described above. Furthermore, the cytokine adjuvant can be administered in the form of an allogeneic cell such as a fibroblast or tumor cell genetically modified to secrete a cytokine such as IL-2, GM-CSF, or other immunostimulatory cytokines The amount of cytokine to administer can be readily determined by one skilled in the art by administering various amounts of cytokine and determining whether an immune response is enhanced, preferably without onset of serious or life-threatening side effects. The cells can be administered in various amounts to provide a desired dose of cytokine. Generally, a cytokine is administered in a dose of at least about 50 units, about 100 units, about 200 units, about 300 units, about 400 units, about 500 units, about 600 units, about 700 units, about 800 units, about 900 units, about 1000 units, about 2000 units, about 3000 units, about 4000 units, about 5000 units, or higher if such a dose enhances an immune response without causing serious or life threatening side effects for the patient. As disclosed herein, an allogeneic fibroblast cell line can be genetically modified to secrete IL-2 and administered in various amounts to give a dose range from 0 to 4000 units of IL-2.

For immuno-gene therapy, the use of allogeneic cells for immunizations obviates the need to establish and genetically modify primary fibroblast and adenocarcinoma such as colon, breast, lung, prostate, pancreas, kidney, endometrium, cervix, ovary, thyroid, or other glandular tissue tumor cultures for each patient. The rationale for the use of allogeneic tumor cells is predicated upon the expression of shared tumor associated antigens (TAA) expressed by both the tumor cells used for immunization and the patients' tumor cells. In colon carcinoma, clonal CTL reactivity has been used to define a number of shared TAAs.

As disclosed herein, a practical allogeneic tumor cell vaccine is developed for the immuno-gene therapy of colon, breast, lung, prostate, pancreas, kidney, endometrium, cervix, ovary, thyroid, or other glandular tissue cancer based on the immunologic profiles of established colon, breast, lung, prostate, pancreas, kidney, endometrium, cervix, ovary, thyroid, or other glandular tissue, respectively, carcinoma cell lines compared to fresh colon, breast, lung, prostate, pancreas, kidney, endometrium, cervix, ovary, thyroid, or other glandular tissue, respectively, carcinoma cultures initiated from biopsy material. The vaccine is composed of tumor cells or lines that are identified on the basis of their secretion of at least one immunosuppressive agent, e.g., TGF-β, are genetically modified to reduce or inhibit the expression of said at least one immunosuppressive agent, e.g., TGF-β, and collectively express a spectrum of tumor associated antigens (TAAs) representative of colon, breast, lung, prostate, pancreas, kidney, endometrium, cervix, ovary, thyroid, or other glandular tissue carcinomas.

Cancer vaccination is the administration of tumor antigens, either in the form of inactivated tumor cells or tumor cell lysate from which the tumor antigens are taken up by antigen presenting cells (APCs) and traffic to lymphoid tissues to stimulate CD8+ cytotoxic T lymphocytes (CTLs) or CD4+ helper (Th) cells of the immune system. With the deification of specific tumor antigens, vaccinations are more often carried out through dendritic cells (DCs) loaded with the relevant protein or peptide or DCs transfected with vector DNA or RNA. Each of these strategies will produce particular effects on the immune system. T cell recognized tumor antigens can be classed either as tumor-specific antigens (TSAs), where the genes encoding the TSA are found only in tumor cells and not in normal tissues, or tumor-associated antigens (TAAs), where the genes encoding the TAA are over-expressed in tumor cells but nonetheless also present at low levels in normal tissues.

TSAs represent perhaps the most desirable targets for anticancer vaccination or adoptive therapy. Their tumor-specific expression precludes any pre-existing immunological self-tolerance as might be found with antigens normally expressed, even at low levels, and thus immune responses directed against TSAs will be unlikely to damage normal tissues. Examples of TSA include the antigens of transforming viruses that cause infected cells to become cancerous, such as the gene products of human papilloma virus (HPV) or Epstein-Barr virus (EBV), and the products of mutated genes expressed only in tumor cells, such as oncogenic RAS and the BCR/ABL fusion protein.

Given the poor presentation of tumor-specific mutated antigens as CTL targets, it turns out that the majority of peptides implicated in CTL responses in cancer patients are tumor-associated antigens. These offer so many viable targets since most tumors are derived from normal tissues, and thus the expression levels of 'self' proteins found in those normal tissues can become elevated, contributing to cancer growth and providing convenient CTL targets. There is no problem with presentation of these TAAs by common HLA alleles.

Colon, breast, lung, prostate, pancreas, kidney, endometrium, cervix, ovary, thyroid, and other glandular tissue carcinomas are known to express a variety of shared TAAs. TAAs include known oncoproteins such as HER-2/Neu and c-MYC (Ben-Mahrez, K. et al. 1988 Br. J. Cancer 57, 529-534; Disis, M. L. et al. 1994 Cancer Res. 54, 16-20; Disis, M. L. and Cheever, M. A. 1996 8, 637-642; Yamamoto, A. et al. 1996 Int. J. Cancer 69, 283-289); tumor suppressor proteins such as p53 (Soussi, T. 2000. Cancer Res. 60, 1777-1788); survival proteins such as survivin and lens epithelium-derived growth factor (LEDGF/p75) (Daniels, T. et al. 2005 Prostate 62, 14-26; Rohayem, J. et al. 2000 Cancer Res. 60, 815-817); cell cycle regulatory proteins such as cyclin B1 (Covini, G. et al. 1997 Hepatology 25, 75-80); mitosis-associated proteins such as centromere protein F (CENP-F) (Covini, G. et al. 1997 J. Hepatol. 26, 255-265; Casiano, C. A. et al. 1995 J. Autoimmun. 8, 575-586; Rattner, J. B. et al. 1997 Clin. Investig. Med. 20, 308-319); chromatin-associated proteins such as topoisomerases (Fernandez Madrid, F. 2005 Cancer Lett. 230, 187-198; Imai, H. et al. 1995 Clin. Cancer Res. 1, 417-424); mRNA-binding proteins such as p62, IMP1, and Koc (Himoto, T. et al. 2005 Int. J. Oncol. 26, 311-317; Zhang, J. Y. et al. 2001 Clin. Immunol. 100, 149-156); and differentiation and cancer testis antigens such as NY-ESO-1 (Stockert, E. et al. 1998 J. Exp. Med. 187, 1349-1354) and Melan-A, SSX2, MAGE-1, MAGE-3, Tyrosinase, and carbonic anhydrase.

Various groups have used "serological proteome analysis" (SERPA) to identify candidate TAAs associated with breast cancer, including the RNA-binding protein regulatory subunit (RS), DJ-1 oncogene, glucose-6-phosphate dehydrogenase (G6PD), heat shock 70-kDa protein 1 (HS71), and dihydrolipoamide dehydrogenase (DLHD) (Canelle, L. et al. 2005 J. Immunol. Methods 299, 77-89; Fernandez Madrid, F. 2005 Cancer Lett. 230, 187-198; Klade, C. S. 2001 Proteomics 1, 890-898; Naour, F. L. et al. 2002 Technol. Cancer Res. Treat. 1, 257-262). The SERPA approach has also been used to identify calreticulin and DEAD-box protein 48 (DDX48) as target autoantigens in pancreatic cancer (Hong, S. H. et al. 2004 Cancer Res. 64, 5504-5510; Xia, Q. et al. 2005 Biochem. Biophys. Res. Commun. 330, 526-532) and the Rho GDP dissociation inhibitor 2 as a major candidate TAA in leukemia (Cui, J. W. et al. 2005 Mol. Cell. Proteomics 4, 1718-1724).

As disclosed herein, both fresh colon carcinoma cell cultures and established colon carcinoma cell lines express a number of previously characterized TAAs including CEA, MUC-1, Ep-CAM, HER-2/neu, the MAGE family, and p53 overexpression. Shawler, D. L. et al. 2002 Clin Exp Immunol. 129, 99-106. CEA is perhaps the best characterized colon carcinoma-associated antigen. It is expressed in 80% of colon cancers, has been demonstrated to be the target of both humoral and cellular immune responses, and contains HLA-A2 binding epitopes.

Ep-CAM is a colon carcinoma-associated cell surface antigen that has been demonstrated to be an important target for both humoral and cellular immunity. MUC-1 is an unusual antigen that can mediate MHC restricted and MHC unrestricted cytotoxicity, presumably through the cross-linking of T cell receptors by repetitive amino acid sequences. HER-2/neu is a well-characterized TAA that can function as an antigen for HLA-A2 directed CTL.

The tumor suppressor gene p53 is abnormally expressed in half of colon carcinomas. A HLA-A2-binding p53 epitope corresponding to a wild type amino acid sequence has recently been identified. Human CTL can target this shared epitope in tumor cells that overexpress p53.

As disclosed herein, the MAGE gene family is frequently expressed in colon carcinomas. MAGE-1 was initially characterized as a tumor-associated antigen in melanoma recognized by CTLs. This initial observation has been extended to include a family of MAGE proteins expressed by tumors of varying histological types. MAGE gene products have been demonstrated to induce potent HLA-A2-restricted CTL Colon, breast, lung, prostate, pancreas, kidney, endometrium, cervix, ovary, thyroid, and other glandular tissue carcinomas are known to express a variety of shared TAAs. As disclosed herein, both fresh colon carcinoma cell cultures and established colon carcinoma cell lines express a number of previously characterized TAAs including CEA, MUC-1, Ep-CAM, HER-2/neu, the MAGE family, and p53 overexpression. CEA is perhaps the best characterized colon carcinoma-associated antigen. It is expressed in 80% of colon cancers, has been demonstrated to be the target of both humoral and cellular immune responses, and contains HLA-A2 binding epitopes.

Ep-CAM is a colon carcinoma-associated cell surface antigen that has been demonstrated to be an important target for both humoral and cellular immunity. MUC-1 is an unusual antigen that can mediate MHC restricted and MHC unrestricted cytotoxicity, presumably through the cross-linking of T cell receptors by repetitive amino acid sequences. HER-2/neu is a well-characterized TAA that can function as an antigen for HLA-A2 directed CTL.

The tumor suppressor gene p53 is abnormally expressed in half of colon carcinomas. A HLA-A2-binding p53 epitope corresponding to a wild type amino acid sequence has recently been identified. Human CTL can target this shared epitope in tumor cells that overexpress p53.

As disclosed herein, the MAGE gene family is frequently expressed in colon carcinomas. MAGE-1 was initially characterized as a tumor-associated antigen in melanoma recognized by CTLs. This initial observation has been extended to include a family of MAGE proteins expressed by tumors of varying histological types. MAGE gene products have been demonstrated to induce potent HLA-A2-restricted CTL PGE2 is a molecule expressed by tumor cells is an immune inhibitory molecule that allows tumor cells to escape immune surveillance.

CTLA4 cytotoxic T lymphocyte antigen 4 is an immune inhibitory molecule that exerts a suppressive effect on the induction of immune responses.

As used herein, the term "immunosuppressive agent" refers to a gene product that has an inhibitory effect on the functions of the immune response. An immunosuppressive agent can interfere, for example, with the function of a cytokine or can inhibit or suppress the immune response by other mechanisms. Immunosuppressive agents are known in the art and include, for example, transforming growth factor-β (TGF-β), vascular endothelial growth factor, prostaglandin E2 (PGE2), interleukin (IL)-10, and IL-6. Also, the protein p15E, mucins, suppressive E-receptor, immunosuppressive acidic protein, and adhesion molecules. It is recognized, for example, that various isoforms of TGF-β exist, and that the immunosuppressive effect of one or more of these isoforms of TGF-β depends, for example, on the target cell. The term "TGF-β" is used generally herein to mean any isoform of TGF-β, provided the isoform has immunosuppressive activity.

As used herein, the term "secrete an immunosuppressive agent" means that the tumor cells secrete a measurable immunosuppressive agent. In cell lines established from colon carcinoma biopsies, TGF-β is secreted with a mean of 480 pg/10 to the power of 6 cells/24 h, and ranging up to 1400 pg/10 to the power of 6 cells/24 h. As used herein, the term "reduce or inhibit the expression of an immunosuppressive agent" is used in its broadest sense to mean that the level of an RNA molecule encoding an immunosuppressive agent or the level or activity of the immunosuppressive agent, itself, is reduced to a level that is less than the level expressed prior to the genetic modification. The terms "reduce" and "inhibit" are both used because, in some cases, the level of expression of an immunosuppressive agent can be reduced to a level that is below the level detectable by a particular assay and, therefore, it cannot be determined whether expression of the immunosuppressive agent is reduced or is completely inhibited. Use of the term "reduce or inhibit" prevents any potential ambiguity due, for example, to the limitations of a particular assay.

Transforming Growth Factor-Beta

The role of transforming growth factor-beta (TGF-β) family members in carcinogenesis is complex. Originally named for their transforming activities in in vitro assays, TGF-βs now unequivocally demonstrate both tumor suppressor and oncogenic activities. In the current paradigm, the suppressor activities dominate in normal tissue, but during tumorigenesis, changes in TGF-β expression and cellular responses tip the balance in favor of its oncogenic activities.

The TGF-β signaling pathway has been the focus of several reviews in the scientific literature. Three TGF-β isoforms are expressed in mammals, TGF-β1, TGF-β2, and TGF-β3, and each is encoded by a unique gene and expressed in both a tissue-specific and developmentally regulated fashion. See, for example, the human cDNA sequence for TGF-β1 (X02812), TGF-β2 (M19154), and TGF-β3 (X14149). TGF-β1 is the most abundant and universally expressed isoform; most studies have either examined or been performed with exogenous TGF-β1. TGF-β is secreted into the extracellular matrix as a latent protein complex bound to a latency-associated protein and one of the four isoforms of latent TGF-β binding protein. Activation of TGF-β, which is required for biologic activity, occurs through poorly understood mechanisms likely involving proteolytic processing of the associated proteins and release of the TGF-β ligand. Once activated, the TGF-β ligands regulate cellular processes by binding to three high-affinity cell surface receptors: the type I TGF-β receptor (TβRI), type II TGF-β receptor (TβRII), and type III TGF-β receptor (TβRIII, also referred to as betaglycan). Where expressed, TβRIII is the most abundant TGF-β receptor and classically functions by binding the TGF-β ligand and transferring it to its signaling receptors, TβRI and TβRII. TβRI and TβRII contain serine/threonine protein kinases in their intracellular domains. TβRI initiates intracellular signaling by phosphorylating a family of transcription factors, the Smads. Smad2 and Smad3 are the receptor-activated Smads for TGF-β because they are phosphorylated by TβRI. Smad4 is a common partner for all of the receptor-activated Smads. Smad6 and Smad7 are inhibitory Smads that block the phosphorylation of Smad2 or Smad3, thus inhibiting TGF-β signaling.

A general mechanism for TGF-β signaling has been elucidated. The TGF-β ligand either binds to TβRIII, which presents TGF-β to TβRII, or binds to TβRII directly. Once bound to TGF-β, TβRII recruits, binds, and transphosphorylates TβRI, thereby stimulating its protein kinase activity. The activated TβRI phosphorylates Smad2 or Smad3, which binds to Smad4. The resulting Smad complex translocates into the nucleus and interacts in a cell-specific manner with transcription factors to regulate specifically the transcription of a multitude of TGF-β-responsive genes. TGF-β signaling is regulated by the level and duration of TGF-β receptor activation, with continuous nucleocytoplasmic shuttling of Smads permitting them to monitor the levels of activated receptors continuously. In addition, TGF-β signaling may be regulated by internalization of the receptors, with some studies suggesting that receptor internalization is required for signaling, and others suggesting a role for internalization in downregulation of signaling. Although TβRI, TβRII, Smad2, Smad3, and Smad4 comprise the core Smad-dependent TGF-β signaling pathway, Smad-independent signaling through mitogen-activated protein kinase (MAPK) signaling pathways, Rho guanosine triphosphatases, PI-3 kinase/Akt, and protein phosphatase 2A has been reported.

Antigene Strategies

At least two different approaches may be utilized for direct gene targeting. The "gold standard" is the gene "knock-out" achieved by homologous recombination (Bronson S K, Smithies O. J Biol Chem 1994; 269:27155-27158). This approach results in the actual physical disruption of the targeted gene as a result of crossover events which occur during cell division between the targeting vector and the gene selected for destruction. Homologous recombination is extremely powerful, but the technique is hampered by the fact that it remains inherently inefficient, time-consuming, and expensive Nevertheless, improvement in the efficiency of this process has been achieved.

A second option for gene targeting employs synthetic oligodeoxynucleotides (ODN) capable of hybridizing with double-stranded DNA. Such hybrids are typically formed within the major groove of the helix, though hybridization within the minor groove has also been reported. In either case, a triple-stranded molecule is produced, hence the origin of the term triple helix-forming oligodeoxynucleotide (TFO). TFOs do not destroy a gene but prevent its transcription either by preventing unwinding of the duplex or preventing binding of transcription factors to the gene's promoter. TFO sequence requirements are based on the need for each base comprising the TFO to form two hydrogen bonds (Hoogsteen bonds) with its complementary base in the duplex. This constrains TFOs to hybridization with the purine bases composing polypurine-polypyrimidine tracks within the DNA. The targeting efficiency of TFOs is further constrained by a number of factors, including need for divalent cations, and perhaps most importantly, by access to DNA compacted within the chromosome structure. Recent experiments from investigators have provided evidence that triple helix formation can occur in living cells, suggesting that these difficulties may ultimately be overcome.

Approaches for the Sequence Specific Knockdown of mRNA

Antisense Oligonucleotides

The notion that small antisense oligonucleotides (ODNs) could be used to specifically inhibit gene expression was first put forth in 1978 by Stephenson and Zamecnik, Proc Natl Acad Sci USA 75: 285 (1978), and Zamecnik and Stephenson, Proc Natl Acad Sci USA 75: 280 (1978). Their studies demonstrated that a tridecamer (13-mer) ODN complementary to terminally repeated sequences in Rous sarcoma virus (RSV) long terminal repeat (LTR) inhibited both RSV translation in a cell-free system and viral replication in cultured cells. It took several years after these elegant experiments for investigators to begin to fully realize the potential of antisense-mediated gene inhibition. With the automation of ODN synthesis in the early 1980s, it became relatively straightforward to obtain ODN s of any sequence and to test their ability to block gene expression via antisense base pairing.

Soon after the demonstration that phosphodiester backbone ODNs were effective as target-specific agents for blocking gene expression, several new backbone modifications were developed to improve the stability of the ODNs and to enhance their effectiveness. The most widely used modification is one in which the nonbridging oxygen is replaced by a sulfur atom, creating phosphorothioate ODNs. This type of backbone formed the basis for the Food and Drug Administration (FDA, Rockville, Md., USA)-approved antisense drug, Vitravene (Isis Pharmaceuticals, Carlsbad, Calif., USA), which targets the cytomegalovirus IE2 mRNA and is used to treat cytomegalovirus-associated retinitis. A second ODN, Genasense, which targets Bcl2 (Genta, Berkely Heights, N.J., USA), has recently completed a phase III clinical trial for metastatic melanoma where it is being used in conjunction with standard chemotherapy, which the antisense potentiates. Several other phosphorothioate antisense ODNs are in earlier stages of clinical trials for a variety of cancers and inflammatory diseases.

The mechanisms of action of ODNs with respect to blocking gene function vary depending upon the backbone of the ODN. Net negatively charged ODNs, such as phosphodiesters and phorphorothioates, elicit RNAse H-mediated cleavage of the target mRNA. Other backbone modifications that do not recruit RNAse H, because of their lack of charge or the type of helix formed with the target RNA, can be classified as steric hindrance ODNs. Popularly used members of this latter group include morpholinos, 2'-O-methyls, 2'-O-allyls, locked nucleic acids and peptide nucleic acids (PNAs). These ODNs can block splicing, translation, nuclear-cytoplasmic transport and translation, among other inhibition targets. It is well beyond the scope of this description to delve further into the mechanisms of action of this diverse array of ODN modifications and for more detailed information, the reader is referred to specific reviews on this subject, which describe each of these modifications in detail.

Ribozymes

Ribozymes are RNA molecules that act as enzymes, even in the complete absence of proteins. They have the catalytic activity of breaking and/or forming covalent bonds with extraordinary specificity, thereby accelerating the spontaneous rates of targeted reactions by many orders of magnitude. The ability of RNA to serve as a catalyst was first shown for the self-splicing group I intron of Tetrahymena thermophila and the RNA moiety of RNAse P. After the discovery of these two RNA enzymes, RNA-mediated catalysis has been found associated with the self-splicing group II introns of yeast, fungal and plant mitochondria (as well as chloroplasts), single-stranded plant viroid and virusoid RNAs, hepatitis delta virus and a satellite RNA from *Neurospora crassa* mitochondria. Ribozymes occur naturally, but can also be artificially engineered for expression and targeting of specific sequences in cis (on the same nucleic acid strand) or trans (a noncovalently linked nucleic acid). New biochemical activities are being developed using in vitro selection protocols as well as generating new ribozyme motifs that act on substrates other than RNA.

The endoribonuclease RNAse P is found in organisms throughout nature. This enzyme has RNA and one or more protein components depending upon the organism from which it is isolated. The RNA component from the *Escherichia coli* and *Bacillus subtilis* enzymes can act as a site-specific cleavage agent in the absence of the protein under certain salt and ionic conditions. Studies of the substrate requirements for human and bacterial enzymes have shown that the minimal substrates for either enzyme resemble a segment of a transfer RNA molecule. This structure can be mimicked by uniquely designed antisense RNAs, which pair to the target RNA, and serve as substrates for RNAse P-mediated, site-specific cleavage both in the test tube and in cells.

It has also been shown that the antisense component can be covalently joined to the RNAse P RNA, thereby directing the enzyme only to the target RNA of interest. Investigators have taken advantage of this property in the design of antisense RNAs, which pair with target mRNAs of interest to stimulate site-specific cleavage of the target and for targeted inhibition of both herpes simplex virus and cytomegalovirus in cell culture.

A number of small plant pathogenic RNAs (viroids, satellite RNAs and virusoids), a transcript from a *N. crassa* mitochondrial DNA plasmid and the animal hepatitis delta virus undergo a self-cleavage reaction in vitro in the absence of protein. The reactions require neutral pH and Mg2+. The self-cleavage reaction is an integral part of the in vivo rolling circle mechanism of replication. These self-cleaving RNAs can be subdivided into groups depending on the sequence and secondary structure formed about the cleavage site. Small ribozymes have been derived from a motif found in single-stranded plant viroid and virusoid RNAs. On the basis of a shared secondary structure and a conserved set of nucleotides, the term 'hammerhead' has been given to one group of this self-cleavage domain. The hammerhead ribozyme is composed of 30 nucleotides. The simplicity of the hammerhead catalytic domain has made it a popular choice in the design of trans-acting ribozymes. Using Watson-Crick base pairing, the hammerhead ribozyme can be designed to cleave any target RNA. The requirements at the cleavage site are relatively simple, and virtually any UH sequence motif (where H is U, C or A) can be targeted.

A second plant-derived, self-cleavage motif, initially identified in the negative strand of the tobacco ringspot satellite RNA, has been termed the 'hairpin' or 'paperclip'. The hairpin ribozymes cleave RNA substrates in a reversible reaction that generates 2',3'-cyclic phosphate and 5'-hydroxyl termini. Engineered versions of this catalytic motif also cleave and turn over multiple copies of a variety of targets in trans. Substrate requirements for the hairpin include a GUC, with cleavage occurring immediately upstream of the G. The hairpin ribozyme also catalyzes a ligation reaction, although it is more frequently used for cleavage reactions.

There have been numerous applications of both hammerhead and hairpin ribozymes in cells for downregulating specific cellular and viral targets. Haseloff and Gerlach, Nature 334: 585 (1988) designed a hammerhead motif in 1988 that can be engineered to cleave any target by modifying the arms that base pair with the target. Another laboratory demonstrated that this hammerhead ribozyme motif had potential therapeutic application based on a study of cells engineered to express an anti-human immunodeficiency virus (HIV) gag ribozyme in which there was virtually complete inhibition of viral gene expression and replication. Since this study, there have been literally thousands of applications of ribozymes targeting cellular and viral targets. A number of comprehensive reviews have been written that survey these applications, and the reader is referred to these for further treatment of this subject.

DNAzymes

A category of site-specific cleaving nucleic agents that has received considerable attention in the past several years is that of catalytic DNAs. Small DNAs capable of site specifically cleaving RNA targets have been developed via in vitro evolution (as no known DNA enzymes occur in nature). Two different catalytic motifs, with different cleavage site specificities, were found via this search. The most commonly used 10-20 enzymes bind to their RNA substrates via Watson-Crick base pairing and site specifically cleave the target RNA, as do the hammerhead and hairpin ribozymes, resulting in 2',3'-cyclic phosphate and 5'-OH termini. Cleavage of the target mRNAs results in their destruction and the DNAzymes recycle and cleave multiple substrates. Catalytic DNAs are relatively inexpensive to synthesize and have good catalytic properties, making them useful substitutes for either antisense DNA or ribozymes.

Several applications of DNAzymes in cell culture have been published including the inhibition of veg F mRNA and consequent prevention of angiogenesis, and inhibition of expression of the bcr/abl fusion transcript characteristic of chronic myelogenous leukemia. A drawback of catalytic DNAs compared to ribozymes is that they can only be delivered exogenously, but they can be backbone-modified, perhaps allowing them to be delivered systemically in the absence of a carrier.

RNAi and siRNAs

RNAi refers to a group of related gene-silencing mechanisms sharing many common biochemical components in which the terminal effector molecule is a small 21-23-nucleotide antisense RNA. One mechanism uses a relatively long, dsRNA 'trigger,' which is processed by the cellular enzyme Dicer into short, 21-23-nucleotide dsRNAs, referred to as siRNAs. The strand of the siRNA complementary to the target RNA becomes incorporated into a multi-protein complex termed the RNA-induced silencing complex (RISC), where it serves as a guide for endonucleolytic cleavage of the mRNA strand within the target site. This leads to degradation of the entire mRNA; the antisense siRNA can then be recycled. In lower organisms, RNA-dependent RNA polymerase also uses the annealed guide siRNA as a primer, generating more dsRNA from the target, which serves in turn as a Dicer substrate, generating more siRNAs and amplifying the siRNA signal. This pathway is commonly used as a viral defense mechanism in plants.

The term siRNA is now generally used whenever the antisense strand is completely complementary to the mRNA target site. The siRNA may consist of two separate, annealed single strands of 21 nucleotides, where the terminal two 3'-nucleotides are unpaired (3' overhang). Alternatively, the siRNA may be in the form of a single stem-loop, often referred to as a short hairpin RNA (shRNA). Typically, but not always, the antisense strand of siRNAs is also completely complementary to the sense partner strand of the si/shRNA.

Recent experiments indicate that in fission yeast, dsRNA encoded by the centromeric DNA also mediates silencing of centromeric heterochromatin, and is dependent on components of the RNAi pathway. Similar RNAi-like mechanisms are involved in silencing of the *Schizosaccharomyces pombe* mating type locus. Chromatin silencing of an endogenous ura4+ gene in trans is initiated by a ura4+ long-stemmed (280 base pairs) hairpin encoded on an extra-chromosomal plasmid requiring both RNAi components and Clr4 (a histone methylase); spreading of heterochromatin through euchromatin requires the *S. pombe* ortholog of Swi6. Moreover, the same mechanism, using naturally occurring siRNAs derived from endogenous transposons, has been implicated in regulating normal host gene expression in *S. pombe* during meiosis.

In mammalian cells, long dsRNAs (usually greater than 30 nucleotides in length) trigger the interferon pathway, activating protein kinase R and 2',5'-oligoadenylate synthetase2. Activation of the interferon pathway can lead to global downregulation of translation as well as global RNA degradation. However, shorter siRNAs exogenously introduced into mammalian cells have been reported to bypass the interferon pathway, although recent evidence suggests this may not always be the case.

The siRNA antisense product can also be derived from endogenous microRNAs. Data drawn from experiments in several paradigm systems, such as the C. elegans lin4/lin14 pathway, suggest the following pathway for microRNA biogenesis and gene regulation in animal cells. The ends of a transcript are removed in the nucleus by an exo III RNAse (Drosha, in human cells), forming a 70 nucleotide pre-micro RNA fold-back intermediate. Pre-microRNAs may be multicistronic, containing multiple hairpins directed against different target RNAs. The pre-microRNA is actively exported to the cytoplasm where Dicer processing trims the hairpin stem and removes the loop and sense strand to create the final 21-23-nucleotide antisense RNAi effector. In contrast to the prototypical si/shRNAs, the sense and antisense stem partner strands are not completely complementary, containing bubbles or bulges; both the structure and thermodynamic properties of the base pairing are critical for proper processing. Moreover, the antisense strand contains mismatches to one or more sites in the 3' untranslated region of the target mRNA, where binding mediates translational repression rather than mRNA degradation. MicroRNAs are widespread phylogenetically and conserved in some instances; they also exhibit temporal and spatial regulation. A recent estimate for the number of human microRNAs is 200-250.

In human cells, experiments with siRNAs and microRNAs indicate that, regardless of the initial form or processing pathway, a final mature 21-23-nucleotide antisense RNA that is completely homologous to the mRNA will direct mRNA cleavage. In general, the effect of mismatches between siRNAs and target sites can vary from almost none to complete abrogation of activity, for reasons that are only partially understood; however, in at least one case, partial homology resulted in mRNA translation inhibition. In this report, an siRNA with target mismatches designed to mimic a prototypical microRNA-target interaction mediated varying degrees of translational repression, depending on both the specific interaction and the number of target sites in the mRNA. Consequently, it is likely that the structural features typical of siRNAs or microRNAs are important for processing and selection of the antisense strand in RISC and have important implications for the design of RNAi-inducing agents.

RNAi can be activated by either exogenous delivery of preformed siRNAs or via promoter-based expression of siRNAs or shRNAs. Thus, RNAi has emerged as a potent mechanism to specifically knockdown mRNA transcripts to a few percent of their original levels by most methods of detection. RNAi appears to be more potent than antisense RNAs, ribozyme or RNAzymes for targeted message destruction, presumably because it exploits cellular machinery that efficiently directs the antisense component to the target mRNA for site-directed cleavage.

Aptamers

Oligonucleotides can not only be potential therapeutics by binding in a complementary fashion to RNA, but they can also be evolved by selection procedure through the systematic evolution of ligands by exponential enrichment (SELEX) with combinatorial nucleic acid libraries to bind to a large number of targets. Such oligonucleotides are named aptamers. They have been selected not only directed against proteins, but also peptides and non-peptide molecules. Their specificity and affinity to targets can be compared to that of antibodies. The potential for the development of aptamers as therapeutics has been reviewed in the scientific literature.

Decoys

A decoy is an oligonucleotide designed according to the nucleic acid consensus sequence recognised by a particular protein such as transcription factors to interfere with the interaction with the genomic DNA target. Transcription factor decoys are molecules that mimic the binding sites for transcription factor proteins, and compete with promoter regions to absorb this binding activity in the cell nucleus. Transcription factor proteins regulate gene expression via binding to specific DNA sequences found in the promoter/enhancer regions of the genes they control. Although most transcription factor binding has been associated with an increase in gene expression, gene suppression has also been described. By blocking transcription factor-chromosomal DNA interaction, decoys provide a powerful means to manipulate the regulation of gene expression, particularly as transcription factors are increasingly understood to alter gene activation during the course of normal and pathologic processes in cell biology.

Intracellular Antibodies

Combining exquisite specificity and high antigen-binding affinity, intrabodies have been used as a biotechnological tool to interrupt, modulate, or define the functions of a wide range of target antigens at the posttranslational level. An intrabody is an antibody that has been designed to be expressed intracellularly and can be directed to a specific target antigen present in various subcellular locations including the cytosol, nucleus, endoplasmic reticulum (ER), mitochondria, peroxisomes, plasma membrane and trans-Golgi network (TGN) through in frame fusion with intracellular trafficking/localization peptide sequences. Although intrabodies can be expressed in different forms, the most commonly used format is a singlechain antibody (scFv Ab) created by joining the antigen-binding variable domains of heavy and light chain with an interchain linker (ICL), most often the 15 amino acid linker (GGGGS)(3) (SEQ ID NO:1) between the variable heavy (VH) and variable light (VL) chains. Intrabodies have been used in research of cancer, $HIV_5$ autoimmune disease, neurodegenerative disease, and transplantation. Taking advantage of the high specificity and affinity of an antibody for its antigen, and of the virtually unlimited diversity of antigen-binding variable domains available for molecular targeting, intrabody techniques are emerging as promising tools to generate phenotypic knockouts, to manipulate biological processes, and to obtain a more thorough understanding of functional genomics.

TGF-β Binding Proteins

The TGF-β type III receptor, also known as betaglycan, is a membrane-anchored-proteoglycan that presents TGF-β to the type II signaling receptor. The extracellular region of this receptor may be shed by cells into the medium. Soluble betaglycan binds TGF-β, but does not enhance binding to membrane receptors. In effect, recombinant soluble betaglycan acts as a potent inhibitor of TGF-β binding to membrane receptors and blocks TGF-β action. This effect is particularly pronounced with the TGF-β2 isoform. Treatment with recombinant TGF-β type III receptor (soluble RIII) inhibited angiogenesis and tumor growth in human breast cancer xenografts and significantly reduced number of metastases in the lung and axillary lymph nodes in this model. Soluble TGF-β receptor II appears to have similar properties and was shown to suppress tumorigenicity in a murine tumor model. Constitutional expression of a soluble TGF-β antagonist, which incorporates in its structure extracellular domain of type II receptor, protects against metastasis in a murine model. Inhibitors targeting TGF-β type I receptor serine-threonine kinase appear to have similar effects.

Tumor Gene-Therapy Strategies

Advances in molecular and tumor biology have contributed greatly to our understanding of the genetic alterations associated with tumor transformation. Thus, gene-therapy strategies have been proposed, which target alterations specific to tumor cells and tumor pathophysiology. These treatment strategies include mutation compensation and immunopotentiation, among others.

Mutation Compensation

Mutation compensation involves correction of the genetic lesions that are aetiologic for neoplastic transformation. This gene-therapy strategy is also known as correctional gene therapy and focuses on functional ablation of expression-dysregulated oncogenes, replacement or augmentation of the expression of tumor-suppressor genes or interferences with signalling pathways of some growth factors or other biochemical processes that contribute to the initiation or the progression of the tumor. The purest examples of this gene-therapy strategy are the restoration of normal function of tumor-suppressor genes and the blocking of oncogene activity. Several approaches have been used in the mutation compensation gene-therapy strategy. These include antisense oligonucleotide, catalytic ribozymes and small oligonucleotides, dominant-negative gene mutation and, most recently, small interfering RNA (siRNA) technology.

Immunopotentiation

Modulation of immune response is particularly attractive as a modality for cancer gene therapy. A key focus of tumor gene therapy is the enhancement of the immune system's ability to destroy tumor cells. Passive immunopotentiation involves boosting the natural immune response to make it more effective. Active immunopotentiation requires the initiation of an immune response against a previously unrecognized tumor. The immunopotentiation gene therapy capitalizes on strategies such as the expression of cytokine genes which may enhance the activity of antigen-presenting cells and T cells, the expression of co-stimulatory molecules, such as B7.1 and B7.2, which facilitate the recognition and killing of tumor cells or the delivery of exogenous immunogens, which generate local inflammatory reactions that increase the ability of antigen-presenting cells to recognize tumor-associated antigens.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

when administered to said patient regardless of tumor type said composition comprising a mixture of two or more different allogeneic tumor cell lines wherein at least one-type of said allogeneic tumor cell lines comprises tumor stem cells, each of tumor cell lines natively secretes an immunosuppressive agent which is TGF-β, PGE-2 or CTLA-4 and has been genetically modified to inhibit the expression of said immunosuppressive agent, wherein the cell lines in said mixture collectively express tumor associated antigens such that of tumor-associated antigens representing all types tumor is presented, wherein said tumor type includes cancers of the colon, breast, lung, prostate, pancreas, kidney, endometrium, cervix, ovary, thyroid, or other glandular tissue carcinomas or melanoma, cancer of the central nervous system or lymphoma.

2. The composition of claim 1, further comprising an allogeneic cell genetically modified to express a cytokine.

3. The composition of claim 2, wherein said cytokine is IL-2.

4. The composition of claim 2, wherein said cytokine expressing allogenic cell is a fibroblast.

5. The composition of claim 1, wherein said genetic modification is by homologous recombination.

6. The composition of claim 1, wherein said genetic modification generates an antisense molecule.

7. The composition of claim 1, wherein said genetic modification generates a ribozyme.

8. The composition of claim 1, wherein said genetic modification generates RNAi or siRNAs.

9. The composition of claim 1, wherein said mixture comprises three or more different tumor cell lines.

10. The composition of claim 1, wherein said mixture comprises four or more different allogeneic tumor cell lines.

11. The composition of claim 10, wherein said mixture comprises five or more different allogeneic tumor cell lines.

12. The composition of claim 11, wherein said mixture comprises six or more different allogeneic tumor cell lines.

13. The composition of claim 12, wherein said mixture comprises eight or more different allogeneic tumor cell lines.

14. The composition of claim 1, wherein said immune response is a CTL response.

15. A method of stimulating an immune response in a cancer-bearing patient comprising administering to said

What is claimed is:

1. A universal tumor vaccine composition that stimulates an immune response to autologous tumor cells in a patient patient the composition of claim 1, whereby said mixture of allogeneic tumor cells stimulates an immune response to said cancer in said patient, wherein said cancer includes cancer of the colon, breast, lung, prostate, pancreas, kidney, endometrium, cervix, ovary, thyroid, or other glandular tissue carcinomas or melanoma, cancer of the central nervous system or lymphoma.

16. The method of claim 15, wherein said immune response comprises a cytotoxic T lymphocyte (CTL) response.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetically constructed interchain linker

<400> SEQUENCE: 1

Gly Gly Gly Gly Ser Gly Gly Gly Gly Ser Gly Gly Gly Gly Ser
1               5                   10                  15
```